(12) United States Patent
Trzecieski (10) Patent No.: US 10,463,812 B2
(45) Date of Patent: Nov. 5, 2019

(54) DEVICE FOR VAPORIZING OF PHYTO MATERIAL WITH MULTIPLE HEATER ELEMENTS AND SENSORS

(71) Applicant: Michael Alexander Trzecieski, Toronto (CA)

(72) Inventor: Michael Alexander Trzecieski, Toronto (CA)

(73) Assignee: Vampium Inc., Toronto (CA)

( * ) Notice: Subject to any disclaimer, the term of this patent is extended or adjusted under 35 U.S.C. 154(b) by 111 days.

(21) Appl. No.: 15/719,400

(22) Filed: Sep. 28, 2017

(65) Prior Publication Data

US 2018/0085539 A1 Mar. 29, 2018

Related U.S. Application Data

(60) Provisional application No. 62/400,716, filed on Sep. 28, 2016.

(51) Int. Cl.

| | |
|---|---|
| *A24F 11/00* | (2006.01) |
| *A24F 47/00* | (2006.01) |
| *A24F 13/00* | (2006.01) |
| *A24F 17/00* | (2006.01) |
| *A24F 25/00* | (2006.01) |
| *A61M 11/04* | (2006.01) |
| *A61M 16/00* | (2006.01) |

(Continued)

(52) U.S. Cl.
CPC ............ *A61M 11/042* (2014.02); *A61L 9/03* (2013.01); *A61M 15/08* (2013.01); *A61M 16/0069* (2014.02); *A61L 9/14* (2013.01); *A61L 2209/111* (2013.01); *A61L 2209/133* (2013.01); *A61M 2205/3368* (2013.01); *A61M 2205/3653* (2013.01); *A61M 2205/50* (2013.01); *A61M 2205/8206* (2013.01)

(58) Field of Classification Search
CPC ............... A24F 47/008; A61M 11/042; A61M 16/0069; A61M 2205/50; A61M 2205/8206; A61M 2205/3368
USPC ................................................... 131/329, 328
See application file for complete search history.

(56) References Cited

U.S. PATENT DOCUMENTS

| | | | | |
|---|---|---|---|---|
| 5,269,327 A | * | 12/1993 | Counts ................. | A24F 47/008 128/200.14 |
| 5,530,225 A | * | 6/1996 | Hajaligol ............. | A24F 47/008 131/194 |

(Continued)

*Primary Examiner* — Abdullah A Riyami
*Assistant Examiner* — Thang H Nguyen
(74) *Attorney, Agent, or Firm* — Bereskin & Parr LLP/S.E.N.C.R.L., s.r.l.

(57) ABSTRACT

A novel device for vaporizing of phyto material is disclosed. The device includes a housing and a heating chamber, wherein the heating chamber is for receiving of phyto material, in first and second phyto material portions. The heating chamber includes a centrally located first heater element disposed on a first substrate and a second heater element disposed on the first substrate, the heater elements for outwardly radiating heat through the phyto material, where at least one of the heating elements is enabled and a user inhales vapor from an inhalation aperture in fluid communication with the heating chamber. An airflow processing member restricts a flow of ambient air into the heating chamber. The first heater element is for heating the first phyto material portion and the second heater element is for heating of the second phyto material portion.

11 Claims, 8 Drawing Sheets

(51) Int. Cl.
*A61M 15/08* (2006.01)
*A61L 9/03* (2006.01)
*A61L 9/14* (2006.01)

(56) References Cited

U.S. PATENT DOCUMENTS

| | | | | |
|---|---|---|---|---|
| 5,665,262 | A * | 9/1997 | Hajaligol | A24F 47/008 219/553 |
| 2013/0255702 | A1* | 10/2013 | Griffith, Jr. | A24F 47/008 131/328 |
| 2014/0060554 | A1* | 3/2014 | Collett | H05B 3/265 131/328 |
| 2015/0216233 | A1* | 8/2015 | Sears | A24F 47/008 362/230 |
| 2018/0020728 | A1* | 1/2018 | Alarcon | G01F 1/696 392/404 |
| 2018/0070641 | A1* | 3/2018 | Batista | A61M 15/0036 |
| 2018/0301915 | A1* | 10/2018 | Colotte | H02J 7/0029 |

* cited by examiner

DEVICE FOR VAPORIZING OF PHYTO MATERIAL WITH MULTIPLE HEATER ELEMENTS AND SENSORS

CROSS REFERENCE TO RELATED APPLICATION

This application benefits from the priority of U.S. Provisional Applications 62/400,716 filed on Sep. 28, 2016, which is incorporated herein by reference.

TECHNICAL FIELD OF THE INVENTION

The technical field relates to a device for vaporization of phyto materials and more specifically to a device for vaporization of phyto material in either phyto form or extract form.

BACKGROUND OF THE INVENTION

Aromatherapy generally uses essential oils, which are extracted from phyto materials, such as leaves of plants, for therapeutic benefits. These essential oils are either massaged into the skin or can be inhaled. In some cases the phyto materials are heated in order to release the essential oils therefrom. By heating these phyto materials at predetermined temperatures, essential oils and extracts are boiled off. Depending upon the temperature at which these phyto materials are heated, an aroma or vapor is given off, which is then inhaled by a user for its therapeutic benefits. Devices that provide such operation are generally known as vaporizers. There are also extracts available that are derived from the phyto material, known as phyto material extracts. These phyto material extracts have a consistency of honey and are typically highly purified forms. Normally these extracts are vaporized at temperatures between 500 to 700 degrees Fahrenheit, whereas phyto material in leaf form is vaporized between 350 and 450 degrees Fahrenheit.

Many conduction vaporizers heat the outside walls of the heating chamber to then heat phyto material that is contained within the heating chamber. Walls of the heating chamber that are on the outside and not contacting the phyto material are typically wrapped in insulating material. In some cases the heat is held by an insulating material, but this results in the heating chamber being less efficient because heat is reflected back inside by the insulation material. There are prior art vaporizers known on the market that also have large heating chambers that can fit approximately 0.8 g of phyto material inside. Unfortunately, these prior art vaporizers are conduction style and if they are not filled completely they do not perform as efficiently and vapor is not properly released from the phyto materials.

It is therefore an object of the invention to overcome the deficiencies in the prior art.

SUMMARY

In accordance with the embodiments of the invention there is provided a device for vaporizing of phyto material comprising: a housing comprising a first end and a second end opposite the first end; a heating chamber coupled with the housing, the heating chamber comprising a first end and a second end opposite the first end, the heating chamber for receiving of phyto material disposed proximate the first end, the phyto material comprising a first phyto material portion and a second phyto material portion, the heating chamber further comprising: a multi segmented heater comprising: a first heater element disposed on a first substrate; a second heater element disposed on the first substrate; a first temperature sensor disposed proximate the first heater element disposed on the first substrate and thermally coupled therewith for providing a first temperature signal and for contacting the first phyto material portion; a second temperature sensor proximate the second heater element disposed on the first substrate and thermally coupled therewith for providing a second temperature signal and for contacting the second phyto material portion; a heater connection port electrically coupled with the first and second heater elements; a temperature sensor connection port electrically coupled with the first and second temperature sensors; a first rechargeable battery; a first control circuit comprising a processor and electrically coupled with the heater connection port and the temperature sensor connection port, wherein the heating chamber is for receiving of the phyto material, wherein the phyto material when inserted into the heating chamber is for contacting of the first and second heater elements, wherein, in use, the first control circuit is for providing of electrical current to at least one of the first and second heater elements and for receiving of the first and second temperature signals, wherein the at least one of the first and second heater elements is for providing heat to the phyto material for forming a vapor, wherein enabling of the first heater element results in heating of the first phyto material portion and enabling of the second heater element results in heating of the second phyto material portion, heat emitted from the first and second heater elements is for being emitted outwardly through the at least one of the first and second phyto material portions and outwards toward an inside surface of the heating chamber that is in contact with the first and second phyto material portions; and, an inhalation aperture in fluid communication with the heating chamber for having the vapor propagate therethrough.

In accordance with the embodiments of the invention there is provided a device for vaporizing of phyto material comprising: a housing comprising a first end and a second end opposite the first end; a heating chamber for receiving of a multi segmented heater comprising a first heater element disposed within a first well formed within a first substrate for receiving of a first portion of phyto material extract; a second heater element disposed within a second well formed within the first substrate for receiving of a second portion of phyto material extract; a heater connection port and a common ground port electrically coupled with the first and second heater elements; an airflow processing member for facilitating inserting of the multi segmented heater therein when the airflow processing member is not coupled with (i.e. uncoupled from) the housing; a first rechargeable battery; a first control circuit comprising a processor and electrically coupled with the heater connection port and the common ground port through a coupling port, wherein, in use, the first control circuit is for providing of electrical current to at least one of the first and second heater elements, wherein the at least one of the first and second heater elements heats up the first portion of phyto material extract and the second portion of phyto material extract, respectively for releasing a vapor therefrom; and an inhalation aperture in fluid communication with the heating chamber for receiving the vapor and for having the vapor and ambient air propagate therethrough.

In accordance with the embodiments of the invention there is provided a device for vaporizing of phyto material comprising: the phyto material comprising a first phyto material portion and a second phyto material portion; a housing comprising a first end and a second end opposite the first end; a heating chamber for being coupled and uncoupled from the housing, the heating chamber having a first end and a second end opposite the first end, the heating chamber comprising a first substrate comprising: a first heater element disposed within the heating chamber and for frictionally engaging the first phyto material portion; a second heater element disposed within the heating chamber and for frictionally engaging the second phyto material portion, the heating chamber being closed at the second end and comprising an inhalation aperture therein and a heater connection port electrically coupled with the first and second heater elements and a temperature sensor connection port; an airflow processing member for being coupled at a first end of the heating chamber for sealing the first end of the heating chamber other than for allowing of restricted ambient airflow into the heating chamber proximate the first end thereof; a first rechargeable battery; a first control circuit comprising a processor and electrically coupled with the heater connection port and the temperature sensor connection port wherein, in use, the first control circuit is for providing of electrical current to at least one of the first and second heater elements, wherein the at least one of the first and second heater elements heats up the at least one of the first portion of phyto material and the second portion of phyto material, respectively, for releasing a vapor therefrom; and an inhalation aperture in fluid communication with the heating chamber for receiving the vapor and for having the vapor and ambient air propagate therethrough, the heating chamber and airflow processing member forming a removable cartridge.

DETAILED DESCRIPTION OF EMBODIMENTS OF THE INVENTION

Figure 1A:
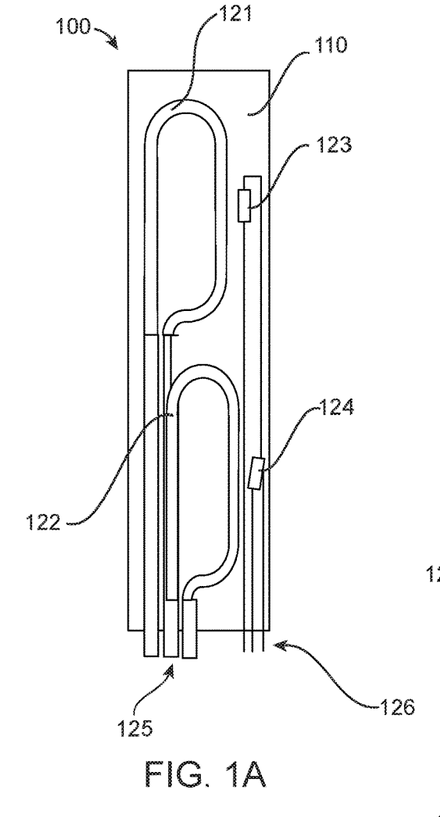
FIG. 1A illustrates a multi segmented heater having first and second heater elements disposed on a first substrate as seen from a top view.
Figure 1B:
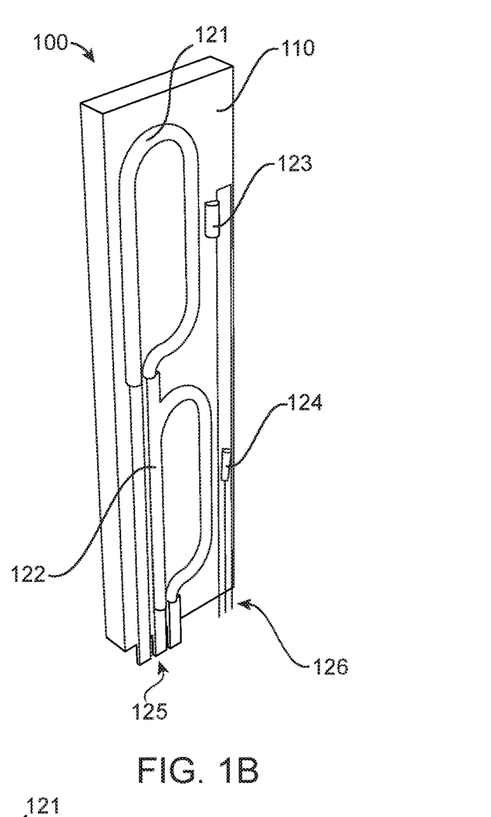
FIG. 1B illustrates a multi segmented heater having first and second heater elements disposed on a first substrate from a perspective view.

FIGS. 1A and 1B illustrate a multi segmented heater 100 as part of the first embodiment of the invention. The multi segmented heater 100 comprises a first heater element 121 disposed on a first substrate 110 and a second heater element 122 disposed on the first substrate 110 and in a first orientation. A first temperature sensor 123 is disposed proximate the first heater element 121, disposed on the first substrate 110 and thermally coupled therewith for providing a first temperature signal based on a temperature of the first heater element 121 and for contacting a first phyto material portion 419*a* (shown in FIG. 3B in the first orientation).

Figure 3A:
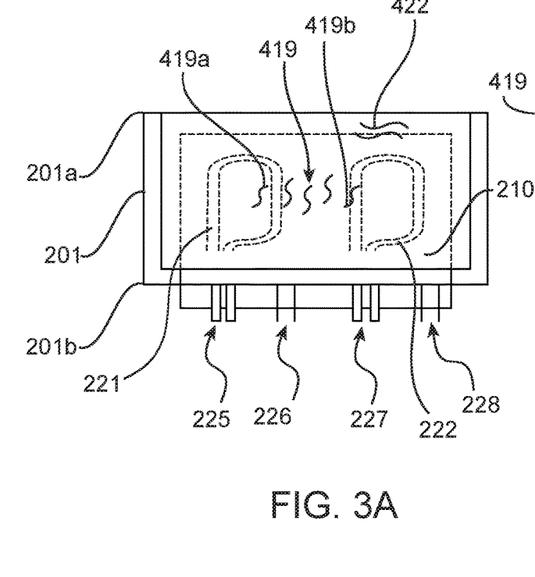
FIG. 3A illustrates the multi segmented heater shown in FIG. 2B disposed within a heating chamber.
Figure 3B:
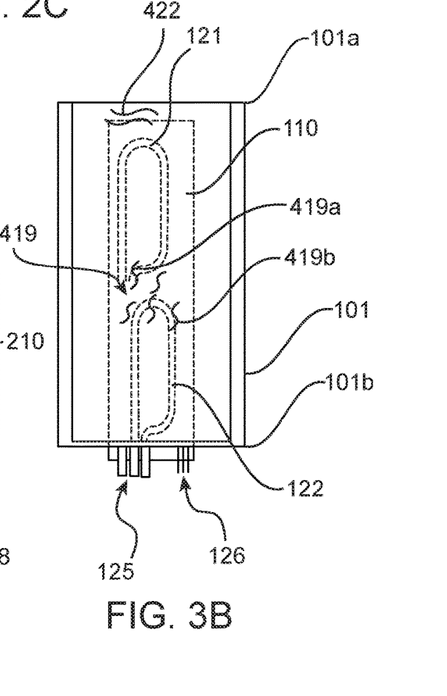
FIG. 3B illustrates the multi segmented heater shown in FIG. 1A disposed within a heating chamber.

The multi segmented heater also includes a second temperature sensor 124, proximate the second heater element 122, disposed on the first substrate 110 and thermally coupled therewith for providing a second temperature signal of the second heater element 122 and for contacting a second phyto material portion 419*b* (shown in FIG. 3B). A heater connection port 125 is provided and electrically coupled with the first and second heater elements 121 and 122. A temperature sensor connection port 126 is electrically coupled with the first and second temperature sensors 123, 124. Together the first phyto material portion 419*a* and the second phyto material portion 419*b* add up to form a phyto material 419. Optionally the heater connection port 125 and the temperature sensor connection port 126 allow for uncoupling of the first and second heater elements 121, 122 and the first and second temperature sensors 123, 124 therefrom. Preferably the temperature sensor allows for a change in resistance in relation to a change in temperature thereof, for example, a diode or a thermocouple is envisaged.

Figure 1C:
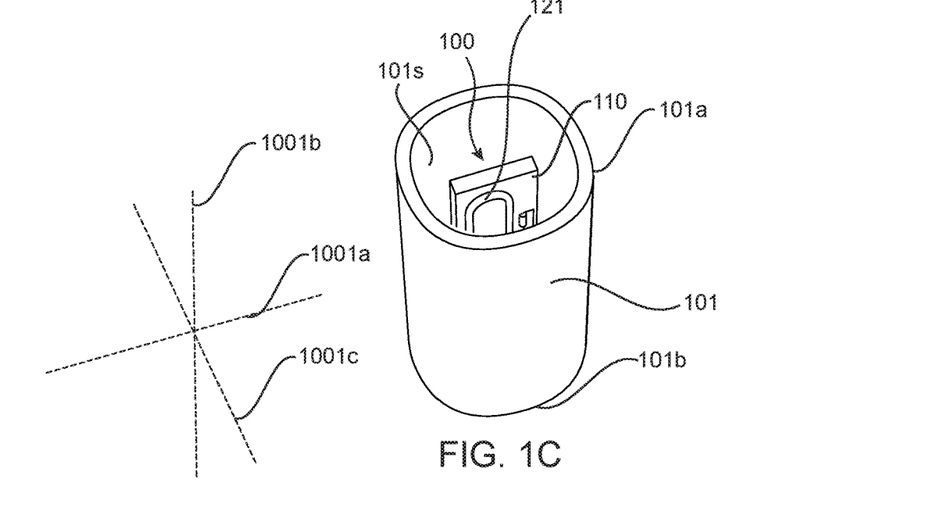
FIG. 1C illustrates a multi segmented heater disposed within a heating chamber in accordance with a first embodiment of the invention.

FIG. 1C illustrates the multi segmented heater 100 disposed within the center of a heating chamber 101, in accordance with the first embodiment of the invention. The first orientation is also known as a "one on top of the other" orientation. Three axes (1001a, 1001b, 1001c) are shown in FIG. 1C to clarify the orientations of the heater elements (121, 122). A first axis 1001a is approximately perpendicular to a second axis 1001b with the first axis 1001a and the second axis 1001b approximately perpendicular to a third axis 1001c. The heating chamber 101 includes a first end 101a and a second end 101b oriented along the second axis 1001b. In addition, the heating chamber 101 comprises an inside surface 101s for contacting the first and second phyto material portions (e.g. portions 419a, 419b shown in FIG. 3B).

Referring to the first axis 1001a, the first heater element 121 is disposed as a single heater element along the first axis 1001a. Referring to the second axis 1001b, the first heater element 121 and the second heater element 122 are disposed along the second axis 1001b, wherein the first heater element 121 is disposed proximate the first end 101a of the heating chamber 101 and the second heater element 122 is disposed proximate the second end 101b of the heating chamber 101. In this embodiment the third axis 1001c is approximately concentric with an inhalation aperture 828 (shown in FIG. 3C) and the first and second heater elements 121, 122 are oriented along the second axis 1001b and primarily radiate heat along the third axis 1001c and towards the inner walls or inside surface 101s of the heating chamber 101.

In accordance with the first embodiment of the invention the first and second heater elements 121 and 122 are oriented vertically along the second axis 1001b. The second axis 1001b is axially oriented with respect to the heating chamber 101 with the second axis 1001b propagating from the first end 101a to the second end 101b thereof. The first and third axes 1001a and 1001c are radial with respect to the heating chamber 101. Both of the first and second heater elements 121 and 122 are for radiating heat along the third axis 1001c. In some embodiments, the first substrate 110 is approximately less than 1 mm in thickness. In a preferred embodiment, the first substrate 110 is about 0.4 mm in thickness.

Figure 2A:
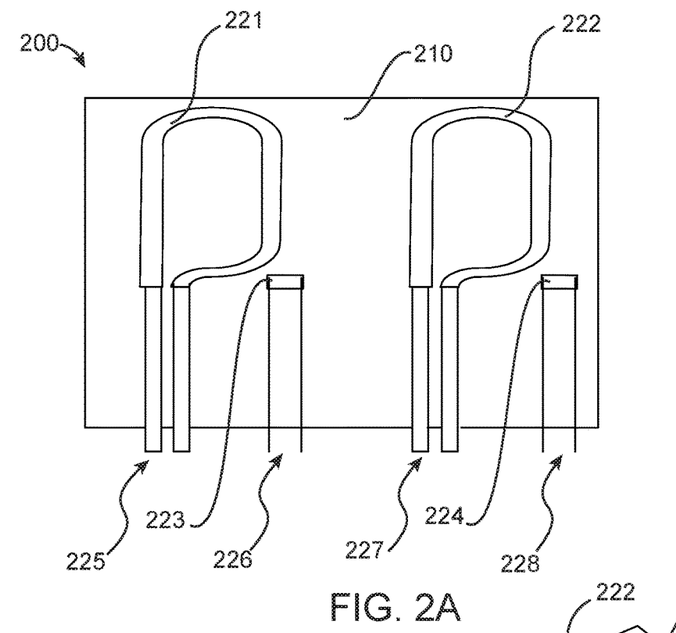
FIG. 2A illustrate a multi segmented heater comprising a first heater element disposed on a first substrate and a second heater element disposed on the first substrate and in a second orientation and in a top view.
Figure 2B:
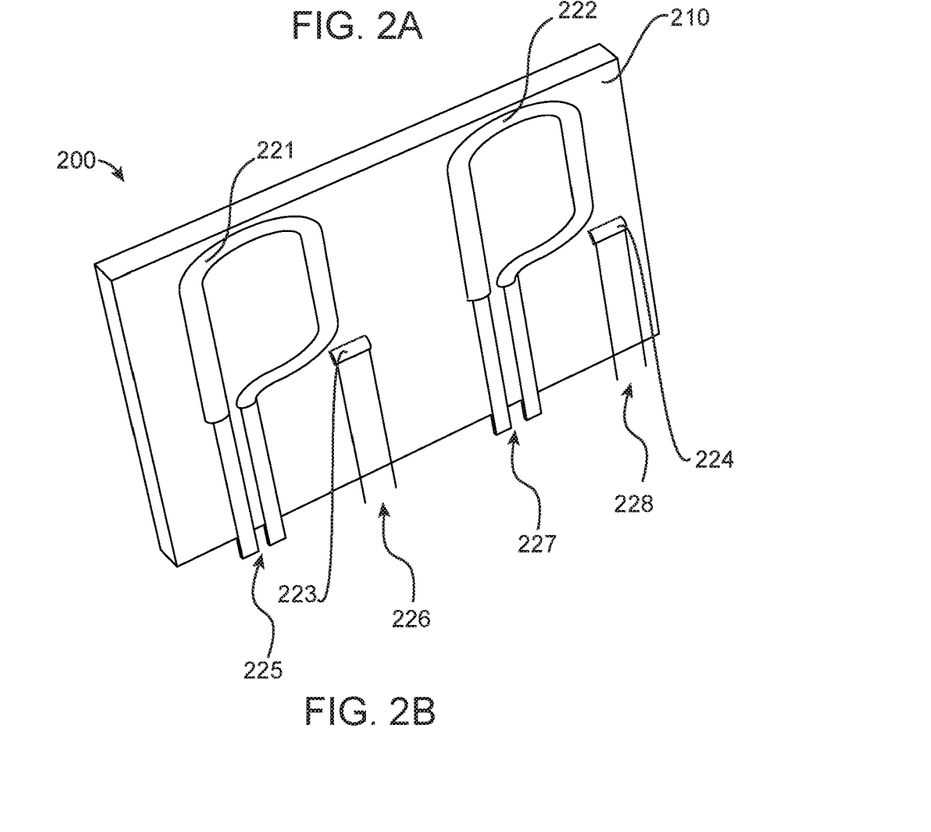
FIG. 2B illustrate a multi segmented heater comprising a first heater element disposed on a first substrate and a second heater element disposed on the first substrate and in a second orientation and in a perspective view.

FIGS. 2A and 2B illustrate a multi segmented heater 200 comprising a first heater element 221 disposed on a first substrate 210 and a second heater element 222 disposed on the first substrate 210 in a second orientation. The multi segmented heater also comprises a first temperature sensor 223 disposed proximate the first heater element 221 and disposed on the first substrate 210 and thermally coupled therewith for receiving of thermal energy therefrom and for providing a first temperature signal for contacting the first phyto material portion 419a (as seen in FIG. 3A).

The multi segmented heater also includes a second temperature sensor 224, proximate the second heater element 222, disposed on the first substrate 210 and thermally coupled therewith for receiving of thermal energy therefrom and for providing a second temperature signal based on the temperature of the second heater element 222 and for contacting the second phyto material portion 419b (shown in FIG. 3A). Heater connection ports 225 and 227 are electrically coupled with the first and second heater element 221 and 222, respectively. A temperature sensor connection port 226 and 228 is electrically coupled with the first and second temperature sensor 223 and 224, respectively. Together the first phyto material portion 419a and the second phyto material portion 419b add up to form the phyto material 419.

Figure 2C:
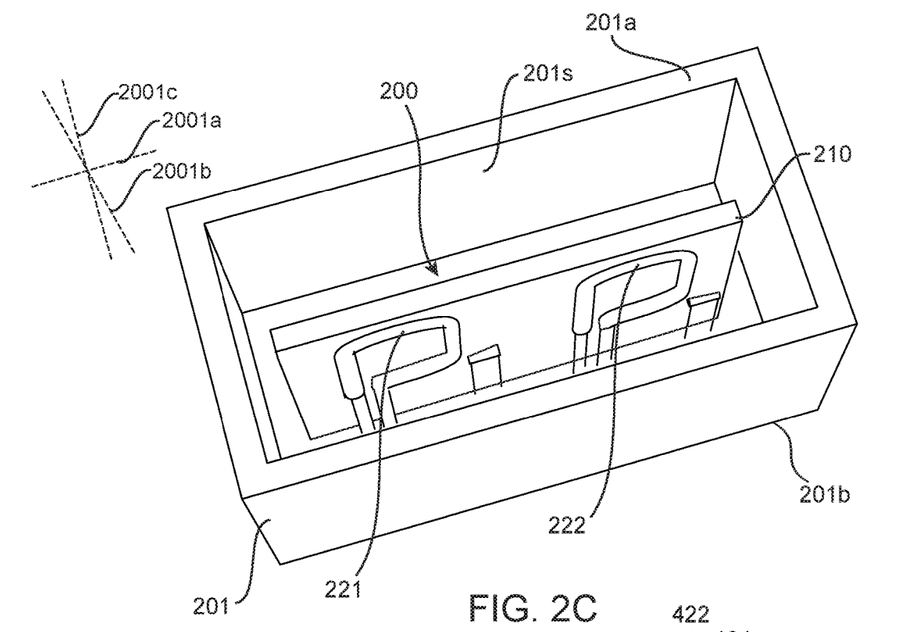
FIG. 2C illustrates a segmented heater as shown in FIG. 2B disposed within a heating chamber in accordance with a second embodiment of the invention.

FIG. 2C illustrates the multi segmented heater 200 disposed within the center of a heating chamber 201 in accordance with a second embodiment. The second orientation of the heater elements is also known as a "side by side" orientation. Three axes (2001a, 2001b, 2001c) are shown in FIG. 2C to clarify the orientations of the heater elements (221, 222). A first axis 2001a is approximately perpendicular to a second axis 2001b with the first axis 2001a and the second axis 2001b approximately perpendicular to a third axis 2001c. The heating chamber 201 includes a first end 201a and a second end 201b oriented along the second axis 2001b. Referring to the first axis 2001a, the first heater element 221 and the second heater element 222 are both disposed along the first axis 2001a and horizontally oriented. Referring to the second axis 2001b, the first heater element 121 and the second heater element are disposed along the second axis 2001b in the side by side orientation within the heating chamber 201. In this embodiment the third axis 2001c is approximately concentric with the inhalation aperture 828 (shown in FIG. 3C) and the first and second heater elements 221, 222 are oriented along the first axis 2001a and primarily radiate heat along the third axis 2001c.

FIG. 3A illustrates the heating chamber 201 according to the second embodiment of the invention with the first and second heater elements 221 and 222 for contacting the first phyto material portion 419a and the second phyto material portion 419b, respectively, of the phyto material 419 that is inserted into the heating chamber 201.

Figure 3C:
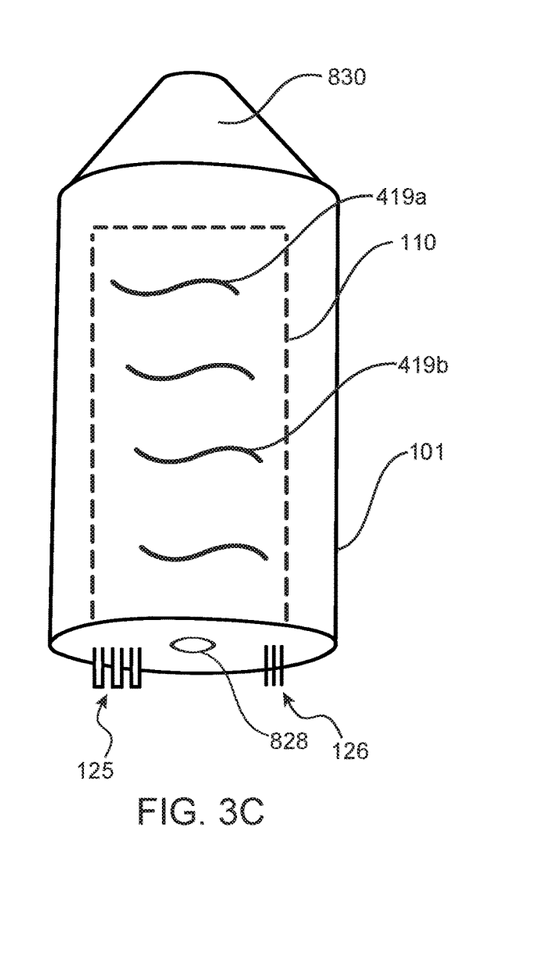
FIG. 3C illustrates a heating chamber prefilled unit with first and second phyto material portions.

FIG. 3B illustrates the heating chamber 101 according to the first embodiment of the invention with the first and second heater elements 121 and 122 for contacting the first phyto material portion 419a and the second phyto material portion 419b, respectively, of the phyto material 419 that is inserted into the heating chamber 101. FIG. 3C illustrates a prefilled heating chamber 101 unit with first and second phyto material portions 419a and 419b packaged within the heating chamber 101 for contacting the first substrate 110 and the inner surface 101s (shown in FIG. 1C) of the heating chamber 101. An airflow processing member 830 restricts a flow of the ambient air from entering the heating chamber 101. Optionally the inhalation aperture 828 is provided for being extended with a tube (see e.g., inhalation aperture 828 in FIG. 6D).

Referring to FIGS. 3A and 2C, it is illustrated in combination how heat, or thermal energy, emitted from the first and second heater elements 221, 222 is being emitted outwardly, in an approximately perpendicular orientation to the first substrate 210 (see e.g. FIG. 2C), through the phyto material portions 419a and 419b toward an inside surface 201s of the heating chamber 201.

Figure 4A:
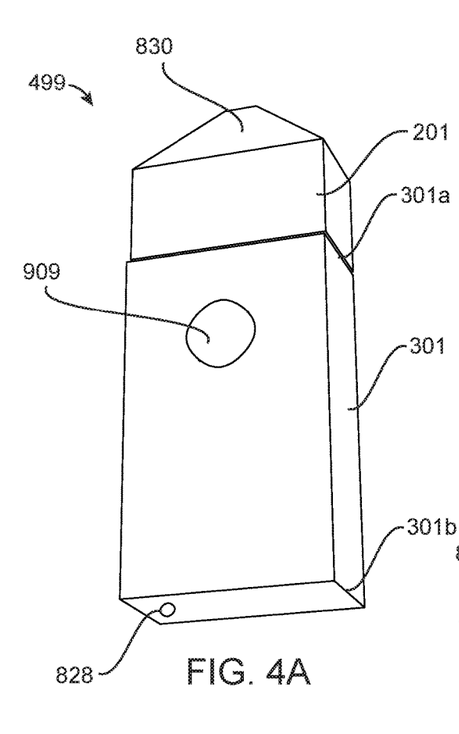
FIG. 4A illustrates a device for vaporizing of phyto material in accordance with a third embodiment of the invention.
Figure 4B:
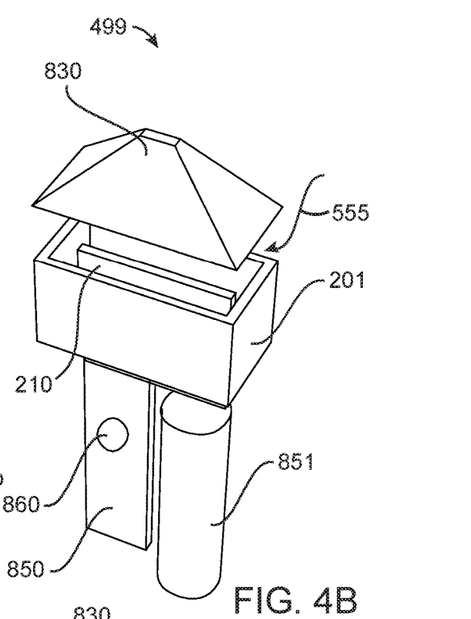
FIG. 4B illustrates a device for vaporizing of phyto material in accordance with a third embodiment of the invention with a housing removed.

FIG. 4A illustrates a perspective view of a device for vaporizing of phyto material 499 in accordance with a third embodiment of the invention. The device 499 comprises a housing 301, the heating chamber 201 in accordance with the second embodiment of the invention proximate a first end 301a of the housing 301, and an inhalation aperture 828 proximate a second end 301b of the housing 301. The inhalation aperture 828 is in fluid communication with the heating chamber 201. FIG. 4B illustrates the device 499 having an airflow processing member 830 for restricting a flow of ambient air 555 into the heating chamber 201 when coupled with the heating chamber 201. When the airflow processing member 830 is uncoupled from the heating chamber 201, the phyto materials 419 can be inserted into the heating chamber 201. In this embodiment the ambient air 555 flows between a controlled spacing of the airflow processing member 830 and where it meets the heating chamber 201 proximate the first end 201a (shown in FIG. 2C) thereof.

FIG. 4B illustrates the device for vaporizing of phyto material 499 in accordance with the third embodiment of the invention with the housing 301 removed. Referring to FIG. 4B, a first rechargeable battery 851 is shown. The battery 851 can be electrically coupled with a first control circuit 850 comprising a processor 860. The first control circuit 850 is electrically coupled with the heater connection port 225 (shown in FIG. 3A) and the temperature sensor connection port 226 (shown in FIG. 3A). As shown in FIG. 4B, the heating chamber 201 can receive the phyto material 419 when the airflow processing member 830 is uncoupled with the heating chamber 201.

Figure 4C:
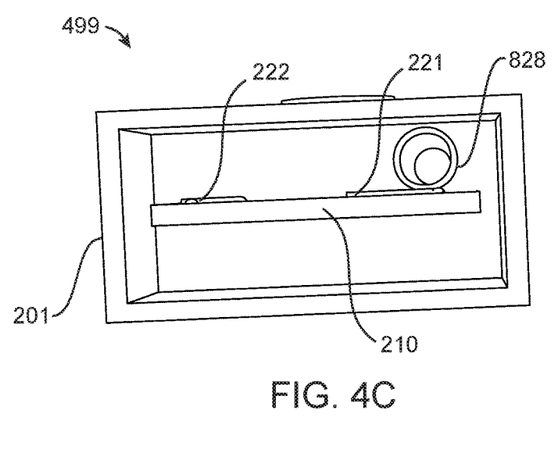
FIG. 4C illustrates a third embodiment of the invention with a first and second heater elements disposed within a heating chamber.
Figure 4D:
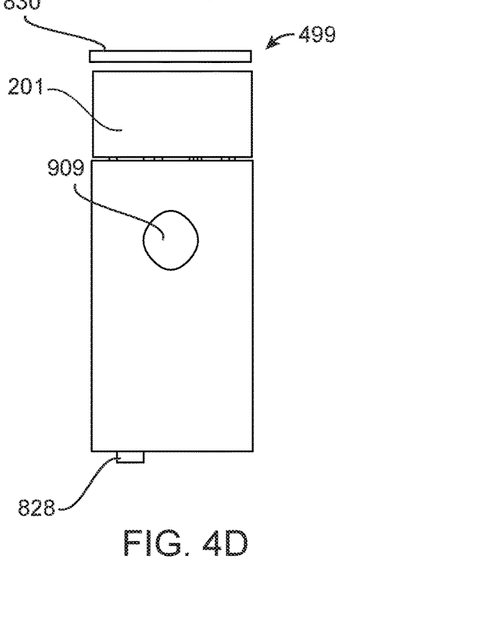
FIG. 4D illustrates a third embodiment of the invention from a side view showing an activation switch.

FIG. 4C illustrates a top view of the device for vaporizing of phyto material 499, with the airflow processing member 830 removed, showing the first and second heater elements 221 and 222 and the inhalation aperture 828. FIG. 4D illustrates a side view of the device 499. An activation switch 909 (shown in FIG. 4A) can be electrically coupled with the first control circuit 850 (see e.g. FIG. 4B) for controlling a provision of electrical power from the first control circuit 850 to the first and second heater elements 221 and 222.

Figure 5A:
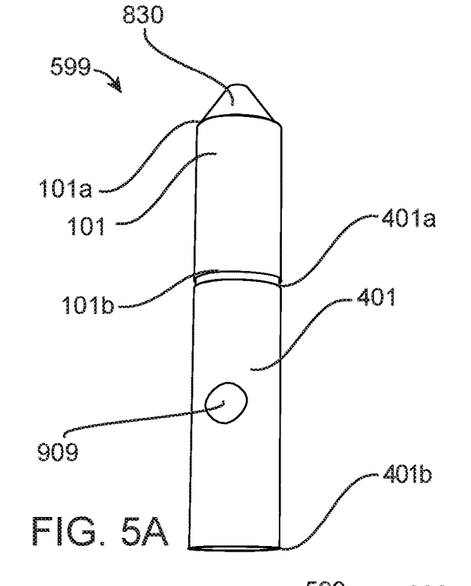
FIG. 5A illustrates a device for vaporizing of phyto material in accordance with a fourth embodiment of the invention.
Figure 5B:
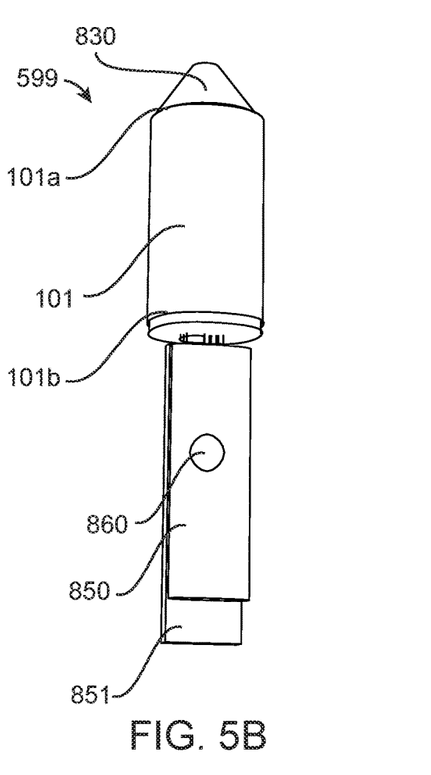
FIG. 5B illustrates a device for vaporizing of phyto material in accordance with a fourth embodiment of the invention with a housing removed.

FIG. 5A illustrates a perspective view of a device for vaporizing of phyto material 599 in accordance with a fourth embodiment of the invention. The device for vaporizing of phyto material 599 comprises a housing 401, the heating chamber 101 in accordance with the first embodiment of the invention proximate a first end 401a of the housing 401, and an inhalation aperture 828 proximate a closed second end 401b of the housing 401. FIG. 5B illustrates the device for vaporizing of phyto material 599 having an airflow processing member 830 for restricting a flow of ambient air into the heating chamber 101 when coupled with the heating chamber 101 proximate the first end 101a. When the airflow processing member 830 is not coupled with the heating chamber 101, the phyto material 419 can be inserted into the heating chamber 101.

FIG. 5B illustrates the device for vaporizing of phyto material 599 in accordance with the fourth embodiment of the invention with the housing 401 removed. Referring to FIG. 5B, a first rechargeable battery 851 is shown and electrically coupled with a first control circuit 850 comprising a processor 860. The first control circuit 860 can be electrically coupled with the heater connection port 125 (shown in FIG. 3B) and the temperature sensor connection port 126 (shown in FIG. 3B). As shown in FIG. 3C, the heating chamber 101 can receive the phyto material 419 when the airflow processing member 830 is not coupled with the heating chamber 101.

Figures 5C, 5D:
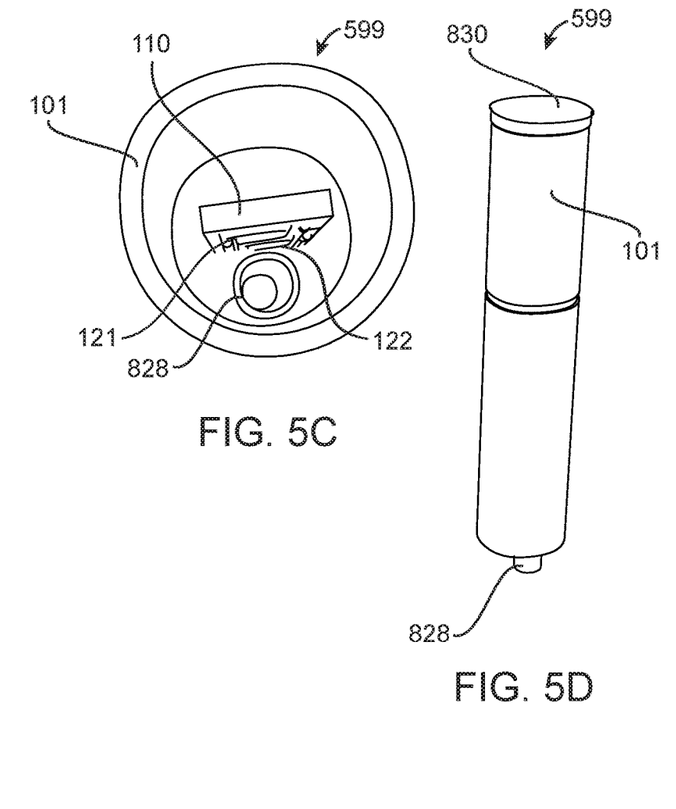
FIG. 5C illustrates a fourth embodiment of the invention showing a first and second heater elements.
FIG. 5D illustrates a fourth embodiment of the invention from a perspective view.

FIG. 5C illustrates a top view of the device for vaporizing of phyto material 599, with the airflow processing member 830 removed, showing the first and second heater elements 121 and 122 and the inhalation aperture 828. FIG. 5D illustrates a side view of the device 599. An activation switch 909 (shown in FIG. 5A) can be electrically coupled with the first control circuit 850 (shown in FIG. 5B) for controlling a provision of electrical power from the first control circuit 850 to the first and second heater elements 121 and 122.

Figure 6A:
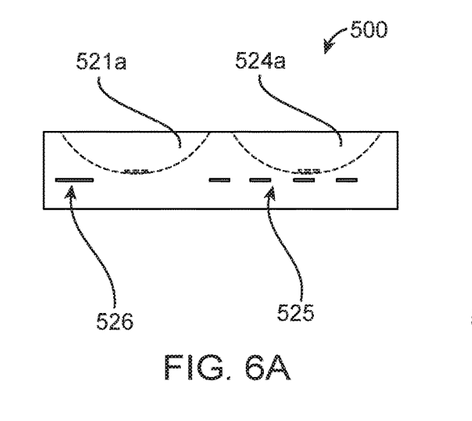
FIG. 6A illustrates a first substrate having first and second heater elements disposed within first and second wells disposed within the first substrate from an end view.
Figure 6B:
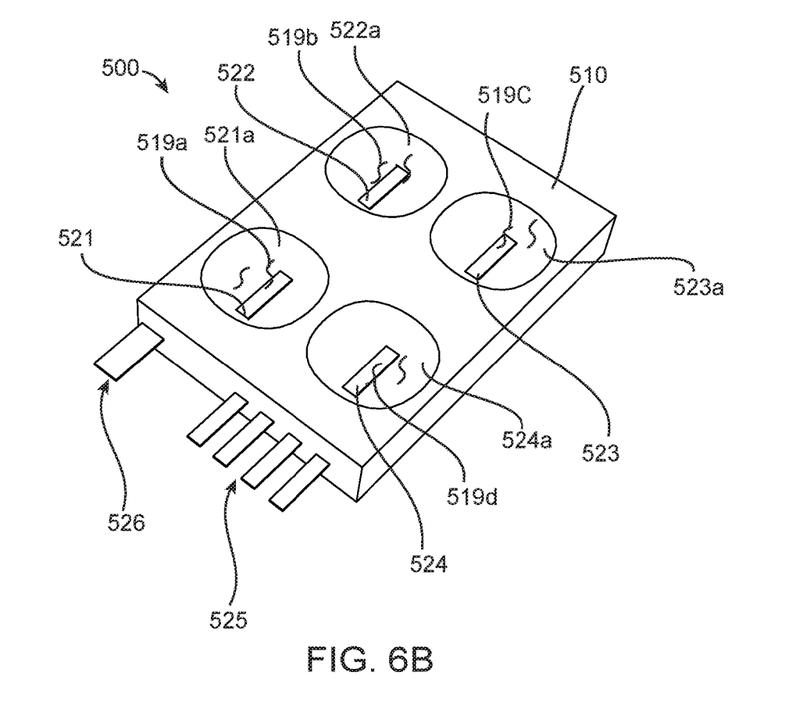
FIG. 6B illustrates a first substrate having first and second heater elements disposed within first and second wells disposed within the first substrate from a perspective view.
Figure 6C:
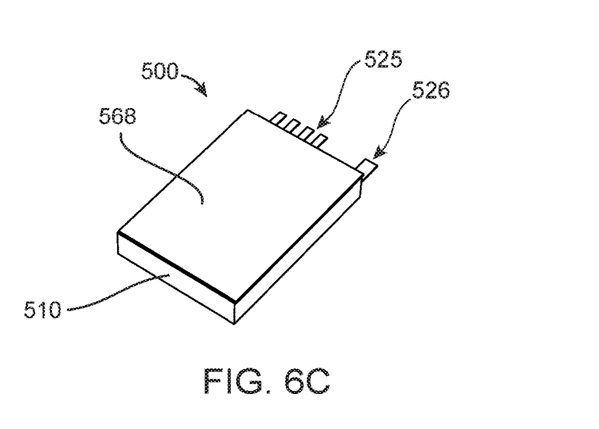
FIG. 6C illustrates a first substrate having first and second heater elements disposed within first and second wells disposed within the first substrate from a bottom perspective view.
Figures 6D, 6E:
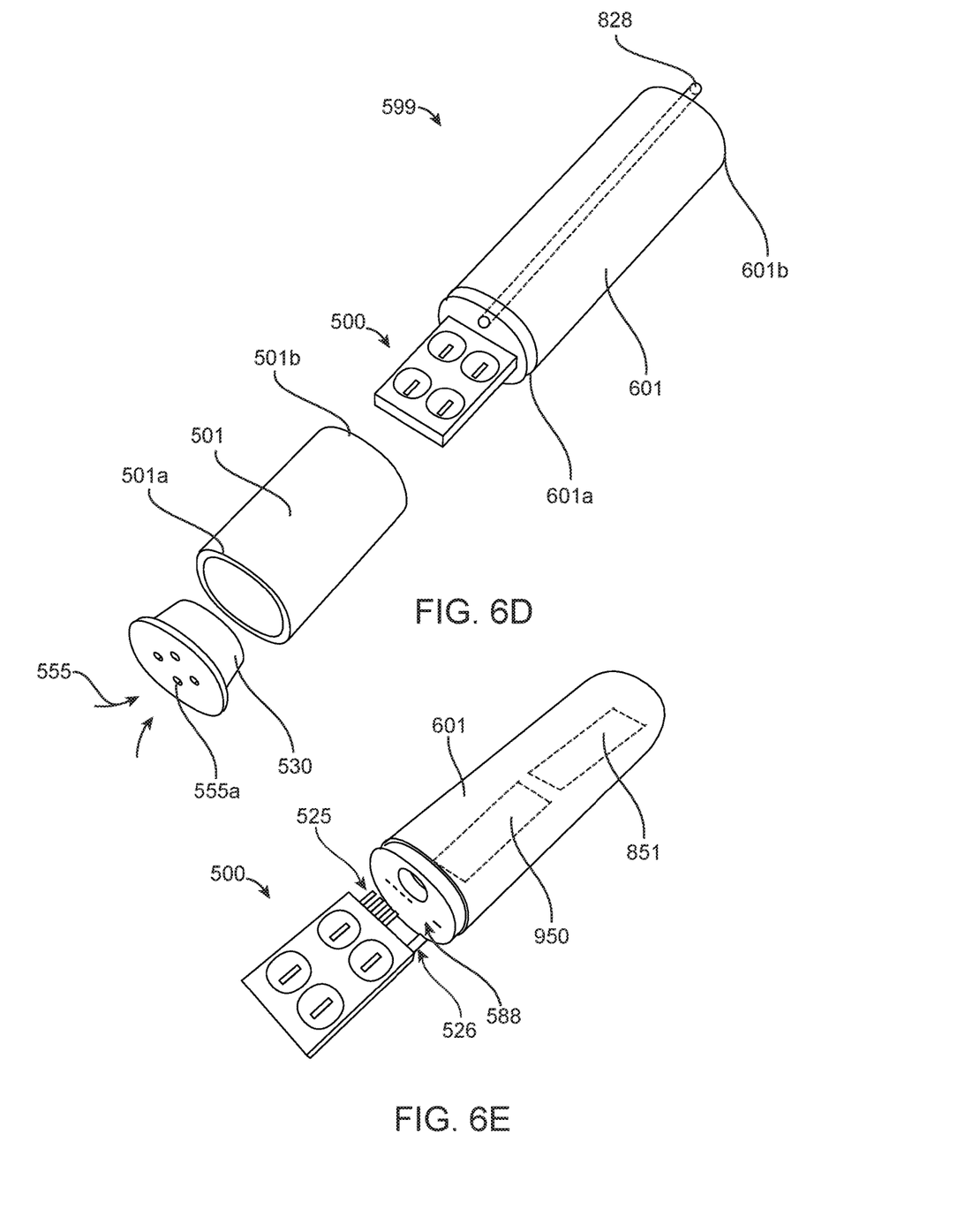
FIG. 6D illustrates a device for vaporizing of phyto material in accordance with a fifth embodiment of the invention and having the first substrate as shown FIG. 6A for use thereby.
FIG. 6E illustrates a heater connection port and a common ground port electrically coupleable with first and second heater elements as part of the first substrate.

FIG. 6D illustrates a device for vaporizing of phyto material 599 in accordance with a fifth embodiment of the invention. The device 599 is formed from a housing 601 comprising a first end 601a and a second end 601b opposite the first end. The device 599 also comprises a heating chamber 501 coupleable with the housing 601 proximate the first end 601a thereof. The heating chamber 501 can receive a multi segmented heater 500 therein. As shown in FIG. 6B, the multi segmented heater 500 comprises a first heater element 521 disposed within a first well 521a formed within a first substrate 510 for receiving a first portion of phyto material extract 519a and a second heater element 522 disposed within a second well 522a formed within the first substrate 510 for receiving a second portion of phyto material extract 519b. In the example embodiment shown in FIGS. 6A and 6B, additional third and fourth wells, 523a and 524a with third and fourth heater elements 523 and 524, respectively, are formed within the first substrate 510. However in this embodiment, only first and second wells 521a, 522a with respective first and second heater elements 521, 522 are necessary for achieving advantages of the fifth embodiment. A first end 501a of the heating chamber 501 is coupleable with an airflow processing member 530 and a second end 501b of the heating chamber 501 is coupleable with the housing 601 proximate the first end 601a thereof. The airflow processing member 530 comprises an umbrella valve for allowing a flow of ambient air 555 into the heating chamber 501 through ambient air input ports 555a in a one way flow and for not allowing a flow of the vapor 422 (see e.g., FIGS. 3A and 3B) to flow back out of the ambient air input ports 555a.

Referring to FIG. 6E, the multi segmented heater 500 also comprises a heater connection port 525 and a common ground port 526 electrically coupled with the first and second heater elements 521 and 522. As shown in FIG. 6D, when the airflow processing member 530 is not coupled with the housing 501, this can facilitate the insertion of the multi segmented heater 500 within the housing 501. FIG. 6D shows an exploded view of the device 599 to illustrate the means in which the airflow processing member 530 couples with the heating chamber 501 and the housing 601.

Referring to FIG. 6E, a first rechargeable battery 851 can be electrically coupled with a first control circuit 950 comprising a processor. The first rechargeable battery 851 and the first control circuit 950 are disposed within the housing 601. The first control circuit 950 can be electrically coupled with the heater connection port 525 and the common ground port 526 of the multi segmented heater 500 through a coupling port 588. As is shown in FIG. 6D, in use, the first control circuit 950 provides electrical current to at least one of the first and second heater elements 521 and 522 wherein the at least one of the first and second heater elements 521 and 522 heats up the first portion of phyto material extract 519a and the second portion of phyto material extract 519b, respectively, for releasing a vapor 422 (see e.g., FIGS. 3A and 3B) therefrom. An inhalation aperture 828 (shown in FIG. 6D) is provided in fluid communication with the heating chamber 501 for receiving of the vapor 422 and for having the vapor 422 and the flow of ambient air 555 propagate therethrough.

Referring to FIG. 6B, the multi segmented heater 500 comprises the first substrate 510. In a preferred embodiment, the first substrate 510 comprises ceramic material and the first and second wells 521a, 522a are formed within the ceramic material and the first and second heater element 521, 522 each comprise a resistive metallic planar heater disposed within a vertex or a center of the first well 521a and the second well 522a, respectively. The resistive metallic planar heater in the first well 521a and the second well 522a is for respectively contacting of the first portion of phyto material extract 519a and the second portion of the phyto material extract 519b, respectively.

Referring to FIG. 6C, the multi segmented heater 500 preferably comprises a foil covering 568. As shown in FIG. 6B, the phyto material extract 519*a*, 519*b*, 519*c*, 519*d* is disposed within the wells 521*a*, 522*a*, 523*a*, 524*a*, respectively. The foil covering 568 is placed on the multi segmented heater 500 to contain the phyto material extract 519*a*, 519*b*, 519*c*, 519*d* within the wells 521*a*, 522*a*, 523*a*, 524*a*, respectively. Prior to inserting the heater connection port 525 and the common ground port 526 of the multi segmented heater 500 into the coupling port 588, the foil covering 568 is removed.

Ceramic is known to be a poor heat transfer medium as well as a poor conductor of electricity. Therefore, the heater elements in accordance with preferred embodiments of the invention are formed from resistive metal traces disposed on ceramic substrates for receiving of electrical current and for heating the substrate in response thereto. Furthermore, when one of heater elements, such as the first heater element 521, is energized, then the phyto material 519*a* contained within the first well 521*a* is vaporized without significantly affecting the phyto material 519*b* contained within the second well 522*a*.

Advantageously, in accordance with the embodiments of the invention, if one of the heater elements of the at least two heater elements disposed on a same substrate should fail, then there is at least one other heating elements that is able to maintain heating of at least a portion of the phyto material within the heating chamber.

Furthermore, a plurality of heater elements are also envisaged that includes more than two heater elements. Accordingly, such an application would be envisaged for use with phyto material extracts in accordance with the fifth embodiment of the invention or potentially with loose leaf phyto materials in accordance with the first and second embodiments of the invention. The fifth embodiment of the invention also allows for use with phyto materials that are of leaf form and not necessarily phyto material extracts.

Referring to the fifth embodiment of the invention, advantageously, having the plurality of wells prefilled with phyto material extract or phyto material and then covered with the foil covering 568 allows for selling of the multi segmented heater 500 as a pre filled unit, where the end user removes the foil covering 568 prior to use. Optionally, the fifth embodiment can also be provided to an end user for filling the multi segmented heater 500 with their own phyto material or phyto material extract into the wells and placing the foil covering 568 thereon for portable use.

Electrical operation of the various heater elements is enabled by the control circuit being operated by an end user. Each well then serves to provide a measured dose. Optionally temperature sensors, as disclosed in the embodiments of the invention, are provided as part of the segmented heater 500 so that heating of the phyto material extract is at predetermined temperatures.

In accordance with embodiments of the invention, multi segmented heaters 500 allow for an amount of phyto material to be loaded into the heating chamber and to have the heating elements enabled as needed to in order to vaporize less than an entire portion, giving the end user more selection. Not vaporizing all of the phyto material at once allows having additional phyto material available for a subsequent vaporization session.

Furthermore, it is envisaged to develop the heating chamber in combination with the first substrate as a pre filled, pre dosed unit that is packaged at a phyto growing facility with phyto material that is preferably ground or with phyto material extract. In this manner, a precise quantity of ground phyto material is inserted into heating chamber. The heating chamber, the first substrate and the heater elements come as a complete unit that is recyclable and allows for being refilled in a similar manner to the way in which prescriptions can be refilled, where a trained person skilled in the art dispenses the phyto materials into each heating chamber within a reasonable degree of error as to offer a precise weighed dose. This allows for wellness specialists to assist patients with their needs by being able to dose what the patient needs in terms of their prescription. Having a removable cartridge with a predetermined dose therein is preferably to wellness practitioners. However, due to environmental factors and costs, it would be advantageous to recycle and sterilize the cartridges and then refill the cartridges with new phyto material or phyto material extract.

Numerous other embodiments are envisaged without departing from the spirit or scope of the invention.

What I claim is:

1. A device for vaporizing of phyto material comprising:
   a housing comprising a first end and a second end opposite the first end;
   a heating chamber coupled with the housing, the heating chamber comprising a first end and a second end opposite the first end, the heating chamber for receiving of phyto material disposed proximate the first end, the phyto material comprising a first phyto material portion and a second phyto material portion, the heating chamber further comprising:
   a multi segmented heater comprising:
   a first heater element disposed on a substrate;
   a second heater element disposed on the substrate;
   a first temperature sensor disposed proximate the first heater element disposed on the substrate and thermally coupled therewith for providing a first temperature signal for and for contacting the first phyto material portion;
   a second temperature sensor proximate the second heater element disposed on the substrate and thermally coupled therewith for providing a second temperature signal and for contacting the second phyto material portion;
   a heater connection port electrically coupled with the first and second heater elements;
   a temperature sensor connection port electrically coupled with the first and second temperature sensors;
   a rechargeable battery;
   a control circuit comprising a processor and electrically coupled with the heater connection port and the temperature sensor connection port, wherein the heating chamber is for receiving of the phyto material, wherein the phyto material when inserted into the heating chamber is for contacting of the first and second heater elements, wherein, in use, the control circuit is for providing of electrical current to at least one of the first and second heater elements and for receiving of the first and second temperature signals, wherein the at least one of the first and second heater elements is for providing heat to the phyto material for forming a vapor, wherein enabling of the first heater element results in heating of the first phyto material portion and enabling of the second heater element results in heating of the second phyto material portion, heat emitted from the first and second heater elements is for being emitted outwardly through the at least one of the first and second phyto material portions and outwards toward an inside surface of the heating chamber that is in contact with the first and second phyto material portions; and, an inhalation aperture in fluid communication with the heating chamber for having the vapor propagate therethrough.

2. The device for vaporizing of phyto material according to claim 1 comprising:
an airflow processing member for restricting a flow of ambient air into the heating chamber when the airflow processing member is coupled with the heating chamber and for allowing for insertion of the phyto materials into the heating chamber when the airflow processing member is uncoupled from the heating chamber.

3. The device for vaporizing of phyto material according to claim 2 wherein the airflow processing member comprises a one way flow valve for allowing of ambient air to enter into the heating chamber and for vapor to other than flow through the one way flow valve.

4. The device for vaporizing of phyto material according to claim 1 comprising:
a first axis approximately perpendicular to a second axis with the first and second axes approximately perpendicular to a third axis, wherein the heating chamber first and second ends are oriented along the second axis, wherein the third axis is approximately concentric with the inhalation aperture and the first and second heater elements are oriented along the second axis and primarily radiate heat along the third axis.

5. The device for vaporizing of phyto material according to claim 1 comprising:
a first axis approximately perpendicular to a second axis with the first and second axes approximately perpendicular to a third axis, wherein the heating chamber first and second ends are oriented along the second axis, wherein the third axis is approximately concentric with the inhalation aperture and the first and second heater elements are oriented along the first axis and primarily radiate heat along the third axis.

6. A device for vaporizing of phyto material comprising:
a housing comprising a first end and a second end opposite the first end;
a heating chamber for receiving of a multi segmented heater comprising:
a first heater element disposed within a first well formed within a first substrate for receiving of a first portion of phyto material extract;
a second heater element disposed within a second well formed within the substrate for receiving of a second portion of phyto material extract;
a heater connection port and a common ground electrically coupled with the first and second heater elements;
an airflow processing member for facilitating inserting of the multi segmented heater therein when the airflow processing member is other than coupled with the housing;
a rechargeable battery;
a control circuit comprising a processor and electrically coupled with the heater connection port and the common ground through a coupling port, wherein, in use, the control circuit is for providing of electrical current to at least one of the first and second heater elements, wherein the at least one of the first and second heater elements and respectively heats up the first portion of phyto material extract and the second portion of phyto material extract for releasing a vapor therefrom; and
an inhalation aperture in fluid communication with the heating chamber for receiving of the vapor for having the vapor and ambient air propagate therethrough.

7. The device for vaporizing of phyto material according to claim 4 wherein the multi segmented heater comprising the substrate comprises ceramic material and the first and second wells are formed within the ceramic material and the first and second heater element each comprises a resistive metallic planar heater respectively disposed at approximately a vertex of the first well and the second well, the resistive metallic planar heater is for respectively contacting of the first portion of phyto material extract and the second portion of the phyto material extract.

8. The device for vaporizing of phyto material according to claim 4 wherein the multi segmented heater comprising the substrate comprises ceramic material and the first and second wells are formed within the ceramic material and the first and second heater element each comprises a resistive metallic planar heater respectively disposed at approximately a vertex of the first well and the second well, the resistive metallic planar heater is for respectively contacting of the first portion of phyto material and the second portion of the phyto material extract.

9. The device for vaporizing of phyto material according to claim 5 wherein the multi segmented heater comprises a foil covering, and the phyto material extract is disposed within the wells and the foil covering is placed thereon to contain the phyto material extract within the wells and wherein prior to insertion of the multi segmented heater connection port and the common ground into the coupling port, the foil covering is removed.

10. The device for vaporizing of phyto material according to claim 4 wherein the airflow processing member comprises an umbrella valve for allowing flow of ambient air into the heating chamber through ambient air input ports in a one way flow and for other than allowing flow of the vapor to flow back out of the ambient air input port.

11. A device for vaporizing of phyto material comprising:
the phyto material comprising a first phyto material portion and a second phyto material portion;
a housing comprising a first end and a second end opposite the first end;
a heating chamber for being coupled and uncoupled from the housing the heating chamber having a first end and a second end opposite the first end, the heating chamber comprising a substrate comprising:
a first heater element disposed within the heating chamber and for frictionally engaging the first phyto material portion;
a second heater element disposed within the heating chamber and for frictionally engaging the second phyto material portion, the heating chamber being closed at the second end and comprising an inhalation aperture therein and a heater connection port electrically coupled with the first and second heater elements and a temperature sensor connection port;
an airflow processing member for being coupled at a first end of the heating chamber for sealing the first end of the heating chamber other than for allowing of restricted ambient airflow into the heating chamber proximate the first end thereof;
a rechargeable battery;
a control circuit comprising a processor and electrically coupled with the heater connection port and the temperature sensor connection port wherein, in use, the control circuit is for providing of electrical current to at least one of the first and second heater elements, wherein the at least one of the first and second heater elements and respectively heats up the at least one of the first portion of phyto material and the second portion of phyto material for releasing a vapor therefrom; and the inhalation aperture in fluid communication with the heating chamber for receiving of the vapor for having the vapor and ambient air propagate therethrough, the heating chamber and airflow processing member forming a removable cartridge.

\* \* \* \* \*